(12) United States Patent
Otto et al.

(10) Patent No.: US 9,295,412 B2
(45) Date of Patent: Mar. 29, 2016

(54) WEARABLE HEALTH MONITORING DEVICE AND METHODS FOR STEP DETECTION

(75) Inventors: Chris A. Otto, Huntsville, AL (US); Xiaofang Chen, Huntsville, AL (US)

(73) Assignee: Integrity Tracking, LLC, Boca Raton, FL (US)

( * ) Notice: Subject to any disclaimer, the term of this patent is extended or adjusted under 35 U.S.C. 154(b) by 238 days.

(21) Appl. No.: 12/192,830

(22) Filed: Aug. 15, 2008

(65) Prior Publication Data
US 2009/0069724 A1 Mar. 12, 2009

Related U.S. Application Data
(60) Provisional application No. 60/956,014, filed on Aug. 15, 2007.

(51) Int. Cl.
*A61B 5/103* (2006.01)
*A61B 5/11* (2006.01)
*A61B 5/00* (2006.01)

(52) U.S. Cl.
CPC ............ *A61B 5/1117* (2013.01); *A61B 5/1118* (2013.01); *A61B 5/6831* (2013.01); *A61B 5/0002* (2013.01)

(58) Field of Classification Search
CPC ........................ A61B 5/1118; G01C 22/006
USPC ........................................................ 600/595
See application file for complete search history.

(56) References Cited

U.S. PATENT DOCUMENTS

| 6,160,478 | A | 12/2000 | Jacobsen et al. |
|---|---|---|---|
| 6,198,394 | B1 | 3/2001 | Jacobsen et al. |
| 7,211,053 | B2 | 5/2007 | Marmaropoulos et al. |
| 8,206,325 | B1 | 6/2012 | Najafi et al. |
| 2002/0118121 | A1* | 8/2002 | Lehrman et al. ........... 340/573.1 |
| 2004/0027246 | A1 | 2/2004 | Aguglia |
| 2004/0059205 | A1 | 3/2004 | Carlson et al. |
| 2004/0077934 | A1 | 4/2004 | Massad |
| 2004/0094613 | A1* | 5/2004 | Shiratori et al. .............. 235/105 |
| 2004/0116822 | A1 | 6/2004 | Lindsey |
| 2004/0199056 | A1 | 10/2004 | Husemann et al. |
| 2006/0031102 | A1 | 2/2006 | Teller et al. |
| 2006/0238333 | A1 | 10/2006 | Welch et al. |
| 2007/0043304 | A1 | 2/2007 | Katayama |

(Continued)

FOREIGN PATENT DOCUMENTS

WO 2006/064397 A2 6/2006

OTHER PUBLICATIONS

Emil Jovanov et al., "A wireless body area network of intelligent motion sensors for computer assisted physical rehabilitation", Journal of NeuroEngineering and Rehabilitation 2005, 2:6, Mar. 1, 2005, 10 pages, source: http://www.jneuroengrehab.com/content/pdf/1743-0003-2-6.pdf.

(Continued)

*Primary Examiner* — Linda Dvorak
*Assistant Examiner* — Emily Lloyd
(74) *Attorney, Agent, or Firm* — Lanier Ford Shaver & Payne, P.C.; Ann I. Dennen

(57) ABSTRACT

A wearable health monitoring device includes at least one sensor for obtaining a signal indicative of movement of a user in at least one axis and logic configured to determine, based upon the signal, whether the user has taken a step.

13 Claims, 11 Drawing Sheets

(56) References Cited

U.S. PATENT DOCUMENTS

| | | | |
|---|---|---|---|
| 2007/0063850 | A1 | 3/2007 | Devaul et al. |
| 2007/0209669 | A1 | 9/2007 | Derchak |
| 2007/0219059 | A1 | 9/2007 | Schwartz et al. |
| 2007/0239229 | A1 | 10/2007 | Masoud et al. |
| 2007/0250286 | A1 | 10/2007 | Duncan et al. |
| 2007/0276270 | A1 | 11/2007 | Tran |

OTHER PUBLICATIONS

D. D. Kouvatsos et al., "Performance Issues in a Secure Health Monitoring Wireless Sensor Network", Performance Modeling and Engineering Group, University of Bradford, Bradford BD7 1DP, UK, 6 pages, source: http://www.comp.brad.ac.uk/het-net/tutorials/WP01.pdf.

Andrew Christian et al., "Gathering Motion Data Using Featherweight Sensors and TCP/IP over 802.15.4", IEEE International Symposium on Wearable Computing, Workshop on On-Body Sensing, Oct. 18-21, 2005, Osaka, Japan, 4 pages, source: http://www.hpl.hp.com/techreports/2005/HPL-2005-188.pdf.

Benny P.L. Lo et al., "Body Sensor Network—A Wireless Sensor Platform for Pervasive Healthcare Monitoring", Department of Computing, Imperial College London, South Kensington Campus, 180 Queen's Gate, London, SW7 2AZ, United Kingdom, 4 pages, source: http://www.pervasive.ifi.lmu.de/adjunct-proceedings/demo/p077-080.pdf.

Emil Jovanov, "Wireless Technology and System Integration in Body Area Networks for m-Health Applications", Electrical and Computer Engineering Department, University of Alabama in Huntsville, Huntsville, Alabama, 3 pages, source: http://www.ece.uah.edu/~jovanov/papers/embs05_integration.pdf.

\* cited by examiner

WEARABLE HEALTH MONITORING DEVICE AND METHODS FOR STEP DETECTION

REFERENCE TO RELATED APPLICATIONS

This application claims priority to Provisional Patent Application U.S. Ser. No. 60/956,014, entitled "Wearable Health Monitoring Device and Methods for Motion Based Feature Extraction" and filed on Aug. 15, 2007, which is fully incorporated herein by reference.

FIELD OF THE DISCLOSURE

The present disclosure relates generally to the field of ambulatory health monitoring, remote monitoring, motion sensing, digital signal processing, and activity monitoring devices. In particular, the present disclosure relates to devices which monitor one or more external signals wherein a change in such signals triggers detection, monitoring, recording, and reporting functions of the system. More particularly, the present disclosure relates to wearable devices to be used for physiological health monitoring, activity assessment monitoring, human state monitoring, categorization of activity, and fall detection.

BACKGROUND OF THE DISCLOSURE

Ambulatory health monitoring devices are known in the field of medical instrumentation, in the field of computing, and in the field of wireless sensor networks. Such devices are used for monitoring, recording, and reporting physiological signals. For example, ambulatory health monitoring devices typically include self-test devices such as weight scales for monitoring a user's weight; blood pressure cuffs for monitoring blood pressure; heart rate monitor for monitoring heart rate; temperature sensors for monitoring skin (or core body) temperature; etc.

Wearable devices form a special sub-class of ambulatory monitoring devices. As a group, these have the added advantage that more continuous data can be collected and data can be collected in the subject's [more] natural environment. Holter monitors for ECG and EEG monitoring are among the first and most frequently used wearable devices. Current devices are limited, however, in that they are strictly data acquisition devices. Data is typically retrieved and analyzed post recording session.

When the devices are wirelessly enabled, they are also in the field of wireless sensor networks (WSNs). WSNs are comprised of one or more sensor nodes and a system controller. Sensor nodes include a computing platform with wireless communication capabilities and one or more sensor devices. The system controller provides a data sync point for the collection and extraction of data, system configuration capabilities, and may include an interface for the end user of the wireless sensor network. The system controller may be referred to as a personal server, network coordinator or personal area network (PAN) coordinator. The system controller may provide visual, audible or other signals to the user in response to certain events.

Another category of health monitoring device includes the so called Personal Emergency Response System (PERS) devices. They are wearable, but strictly speaking are not monitoring any health information. Instead, they are an active alert response system. That is, the user must press an emergency button to notify the monitoring center of an event. This is intended for situations such as when the user falls and needs outside assistance especially suited for independently living elderly adults. These systems have the distinct disadvantage that they require active participation from a user to be effective.

Certain measures of a user activity are often considered important and relevant to the field of interest, but are not all available by current state of the art devices. These are defined herein: Fall Detection refers to the passive detection (no button requires pressing) of a user falling down. Step Detection refers to the systematic detection of steps as well as recording number of daily steps. Orientation or posture refers to whether the user is horizontal or vertical. Category of Activity, for purposes within, refers to whether the user is resting, standing/sitting, walking, or fast walking/running. Sleep/Wake patterns refer to more general categories of activity (sleeping or not sleeping). Levels of Activity refer to any quantitative measure of activity such as caloric expenditure or some other relative units for measuring activity.

SUMMARY OF THE DISCLOSURE

The present disclosure is directed to a wearable device intended for monitoring multiple physiological signals, recording metrics of health, and extracting measures of user state, user context, and categorizing activity.

The present disclosure discloses a novel wearable health monitoring device for the purpose of monitoring, recording, and reporting relevant changes in physiological signals or motion. The device includes a microprocessor (or digital signal processor) at least one sensor for monitoring physiological data, a memory component for storing and retrieving information, and a means to communicate the data. When one sensor is a multi-axis accelerometer, methods are disclosed for extracting a number of pertinent motion-based features including activity estimation, fall detection, step detection, discerning the categories of a user's activity, and recognizing sleep/wake patterns.

Feature extraction refers to the process of analyzing the signals, either post-session or, more desirably, in real-time as raw data is collected, and interpreting the raw signals to extract more useful, application-level, signals or events. For example, heart rate and respiration rate can be extracted from a raw electrocardiogram (ECO); core body temperature can be extracted from skin temperature. In particular, the disclosure disclosed within extracts a number of features from 3-axis accelerometer signals such as user orientation (posture), discerning category of activity, sleep/wake patterns, step detection, estimating levels of activity, and determining when the user falls (fall detection). Activity-induced Energy Expenditure (AEE) refers to a measure of physical activity and close approximation to caloric expenditure.

For purposes of summarizing the disclosure, certain aspects, advantages, and novel features of the disclosure have been described herein. It is to be understood that not necessarily all such advantages can be achieved in accordance with any one particular embodiment of the disclosure. Thus, the disclosure may be embodied or carried out in a manner that achieves or optimizes one advantage or group of advantages as taught herein without necessarily achieving other advantages as may be taught or suggested herein.

These and other embodiments of the present disclosure will also become readily apparent to the those skilled in the art from the following detailed description of the embodiments having reference to the attached figures, the intention not being limited to any particular embodiment or embodiments disclosed.

BRIEF DESCRIPTION OF THE DRAWINGS

The present disclosure is described with reference to the accompanying drawings.

DETAILED DESCRIPTION

Ambulatory health monitoring can have many advantages including frequent monitoring of health metrics, monitoring in the user's natural setting, early detection of abnormal physiological levels, and building a history of user's health information. In addition, measures of an individual's activity (Activity-induced Energy Expenditure), number of daily steps, and their sleep/wake patterns are also generally deemed useful measures of health information. Certain high need individuals, such as seniors living alone or individuals with chronic illnesses, may realize the greatest benefit of ambulatory monitoring. Self-test devices such as thermometers, manual measurement of heart rate, and pedometers can be employed to generate data related to ambulatory monitoring. A comprehensive health monitoring device equipped with the ability to continuously monitor and assess activity could provide greater benefit to individuals wearing the device.

The present disclosure provides a wearable device which includes either a microcontroller or digital signal processor (DSP), a battery, a battery management and power distribution system, and at least one physiological sensor from the following list: electrodes for monitoring cardiac and other muscular activity; oxygen saturation sensors ($SpO_2$); galvanic skin response (GSR) sensors; multi-axis accelerometer for monitoring motion; angular rate sensor (or gyroscope); temperature sensor.

Figure 1:
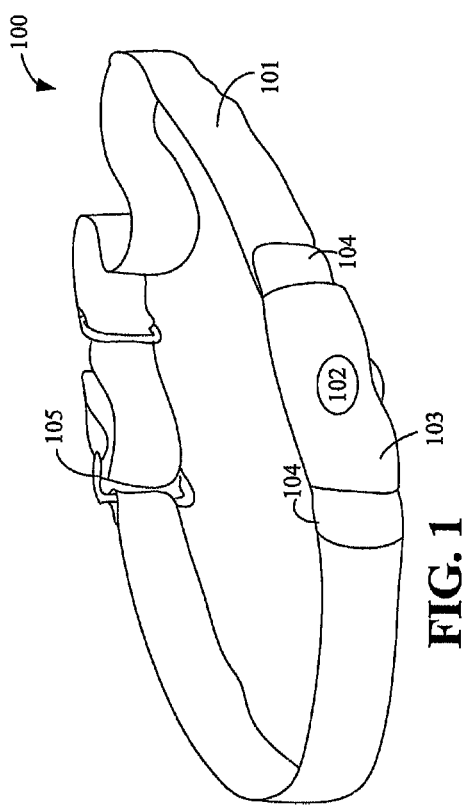
FIG. 1 is a perspective frontal view of an exemplary wearable health monitoring device in accordance with an embodiment of the present disclosure.

FIG. 1 depicts an exemplary perspective view of a wearable health monitoring device 100 in accordance with an embodiment of the present disclosure. The wearable health monitoring device 100 comprises a controller housing 103 and a strap 101, e.g., an elastic strap. The controller housing 103 attaches to the strap 101 with two or more electrode snaps 104. The snaps 104 serve a dual purpose to both attach and secure as well as provide electrical connection to the elastic strap's electrodes, which is described further herein with reference to FIG. 2. The wearable health monitoring device 100 further comprises a connector 105 for fastening and/or tightening the elastic strap 101 around a user's torso.

Note that the controller housing 103 may be comprised of any type of suitable material known in the art or future-developed, including plastic. In one embodiment of the wearable health monitoring device 100, the controller housing 103 is comprised of a water resistant type of material. Thus, the wearable health monitoring device 100 can be used during bathing or swimming.

In one embodiment, the wearable health monitoring device 100 is perpetually in an activated state, i.e., powered on. The controller housing 103 further comprises an actuator 102 for signaling a remote device (not shown). The actuator 102 may be, for example, a button or a switch that when actuated generates a message which is wirelessly transmitted to the remote device, which is described further with reference to FIG. 3.

Figure 2:
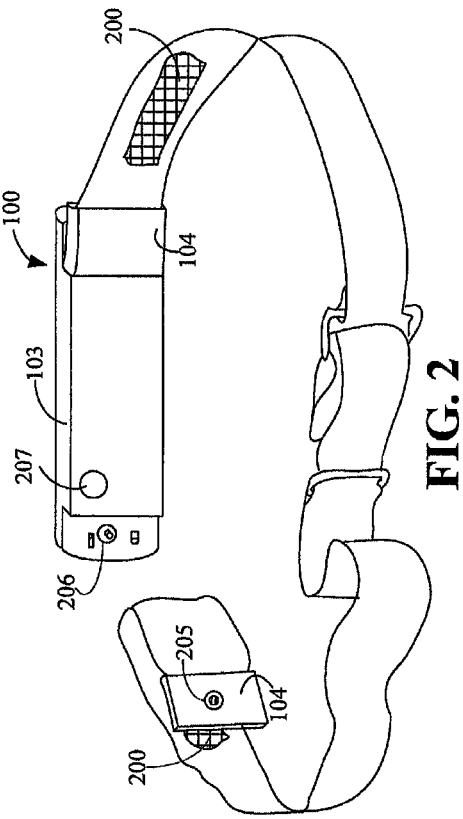
FIG. 2 is a perspective rear view of the wearable health monitoring device depicted in FIG. 1.

FIG. 2 depicts an exemplary perspective view of a back side of the wearable health monitoring device 100. The wearable health monitoring device 100 comprises one or more dry fabric electrodes 200 embedded within the strap 101. In one embodiment, the electrodes 200 are made of conductive polymer yarn and formed in a mesh. Each of the electrode snaps 104 comprise on one side a snap female receptacle 205, which mates with the controller housing snap male connector 206. Therefore, the electrode snaps 104 are removeably attached to the controller hosing 103 by inserting the male connector 206 into the female connector 205.

Each dry fabric electrode 200 embedded in the strap 101 is connected to the female connector 205. In one embodiment, the female connector 205 is riveted through the mesh dry fabric electrode 200 thereby establishing an electrical connection between the electrode 200 and the female connector 205.

Furthermore, the male connector 206 is conductively connected to a printed circuit board (PCB) (not shown) within the controller housing 103. Thus, when the male connector 206 is inserted within the female connector 205, and electrical connection is made between the dry fabric electrodes 200 and the PCB. In this regard, electrical signals picked up by the mesh dry fabric electrodes 200 are transmitted through the female connector 205, the male connector 206 and to the PCB.

In one embodiment the wearable health monitoring device 100 further comprises one or more metal contacts 207. The metal contact 207 is conductively coupled to a thermistor (not shown) on the PCB, which detects temperature. In addition, the metal contact 207 further serves as a third lead of an electrocardiogram (ECG) signal.

In this regard, the first and second electrodes 200 serves as the differential leads of the ECG signal and are biopotential electrodes for measuring biopotentials of the body and generating electrocardiogram (ECG) measurements. In such an embodiment, the electrodes 200 can be placed so they are across a user's heart, and a differential measurement is used to obtain and record ECG data. In such an embodiment, the metal contact 207 serves as the third lead when obtaining the ECG data.

In addition, the electrodes 200 may be used to detect a heartbeat of the user. Notably, heartbeat detection can be extracted in any manner known or future-developed. In one embodiment, the electrodes 200 detect a user's heartbeat through R-peak detection. This can be in the form of hardware or software detection of the maximum peak waveform contained in the deflections in the tracing of the electrocardiogram (ECG), comprising the "Q," "R," and "S" waves, also referred to as the QRS Complex. The "Q," "R," and "S" waves represent the respective ventricular activity of a Heart (not shown). As an example, in real-time the wearable health monitoring device 100, via the electrodes 200, measures the elapsed time between each R-peak (hereinafter referred to as an "R-peak interval"), and the instantaneous heart rate may be calculated as the inverse of the measured R-peak interval.

The ECG data can be extracted from any various number of electrode configurations ranging from two to twelve electrodes. The use of three electrodes (two dry fabric 200 and one metal 207) in FIG. 2 is for exemplary purposes only, and other numbers of electrodes in other embodiments are possible.

In one embodiment, the electrodes 200 may be used to obtain respiration rate. In such an embodiment, the ECG signal is used to extract respiration rate using a low frequency response filter (not shown). The wearable health monitor device 100 performs such extraction by employing a low pass filter (LPF) (not shown) and determining the period of a signal (not shown) transmitted by the LPF. The low pass filter can be implemented in hardware, in DSP firmware, or microcontroller software.

In one embodiment, the wearable health monitoring device 100 analyzes a magnitude of the QRS complex in the time domain and extracts a magnitude of the R-peak as a function of time using the electrodes 200. The wearable health monitoring device 100 then analyzes the derived signal to determine the period (detecting relative maximum), indicative of a respiration rate.

In one embodiment, the wearable health monitoring device 100 extracts measures of Heart Rate Variability (HRV). There are a number of accepted methods for representing HRV including time domain (standard deviation) and frequency domain representation. Notably, such an embodiment uses any suitable process known in the art of future-developed to represent the HRV. The wearable health monitoring device 100 calculates the HRV in system or during post-analysis by analyzing a time series of heartbeats.

Figure 3:
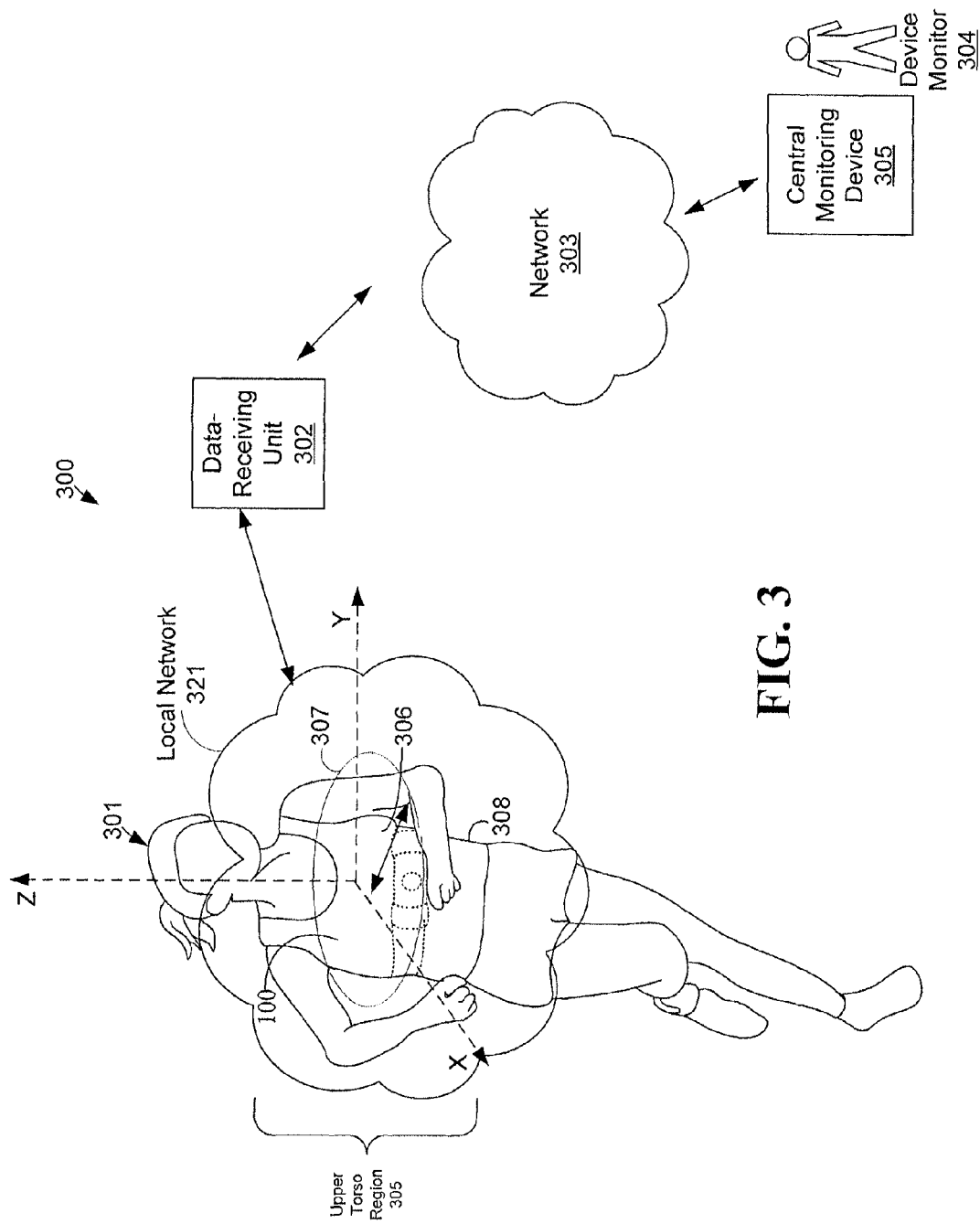
FIG. 3 is a perspective view of a runner donning the wearable health monitoring device depicted in FIG. 1 and a system in accordance with an embodiment of the present disclosure.

FIG. 3 depicts a system 300 in accordance with an embodiment of the present disclosure. The system 300 comprises the wearable health monitoring device 100, as depicted in FIGS. 1 and 2, which is being worn by a user 301. In addition, the system 300 comprises at least one data-receiving unit 302. In such an embodiment, the wearable health monitoring device 100 communicates with the data-receiving unit 302 over a local network 321, e.g., Zigbee.

In addition, the data-receiving unit 302 and/or the monitoring device 100 communicates with a central monitoring device 305 via a network 303. The network 303 may be any type of network known in the art of future-developed. The network 303 may be, for example, broadband over power lines (BPL), optical fiber, Ethernet, a local area network (LAN), a wireless local area network (WLAN), or a wide area network (WAN). Further, the data-receiving unit 302, the wearable health monitor 101, and the central monitoring device 305 comprise hardware and/or software (not shown) known in the art or future-developed for communicating over the networks 321 and 303, which is described further herein.

In the system 300, the user 301 wears the wearable health monitoring device 100. As depicted in FIG. 3, one exemplary location of the wearable health monitoring device 100 is above the user's waist 308 so that a static response (due to gravity) is in relation to an upper torso region 305 of the user 301. As described hereinabove, mounting the wearable health monitoring device 100 is accomplished by wrapping the elastic strap 101 (FIG. 1) around the user's chest 307 and connecting the elastic strap 101 via the connector 105 (FIG. 1). Note that the health monitoring device 100 is worn around the chest 307 next to the skin, i.e., under the clothes of the user 301.

During operation, the wearable health monitoring device 100 transmits physiological data to the data-receiving unit 302. The device 100 may transmit the physiological data to the data-receiving unit 302 upon request, continuously, or automatically at predetermined intervals. The data-receiving unit 302 receives the physiological data and generates historical health data related to the user 301 or detect particular events based upon the physiological data received from the monitoring device 100.

As indicated hereinabove, the system 300 further comprises the central monitoring device 305. The central monitoring device 305 may be substantially similar to the data-receiving unit 302. However, in such an embodiment, the wearable monitoring device 100 provides real-time physiological data related to the user 300 to a device monitor 304, e.g., an individual, via the central monitoring device 305.

During operation, if an event occurs, e.g., there is a change in the user's respiration or heartbeat, the central monitoring device 305 displays data indicative of the event on a graphical user interface (GUI) (not shown). Based upon the displayed data, the device monitor 304 can take an action based upon the physiological data indicative of the event, e.g., call emergency personnel for the user 301.

Note that in the embodiment shown in FIG. 3, the device monitor 304 is depicted graphically as a person. However, the central monitoring device 305 may automatically, upon receipt of the physiological data, electronically notify emergency personnel.

Figure 4:
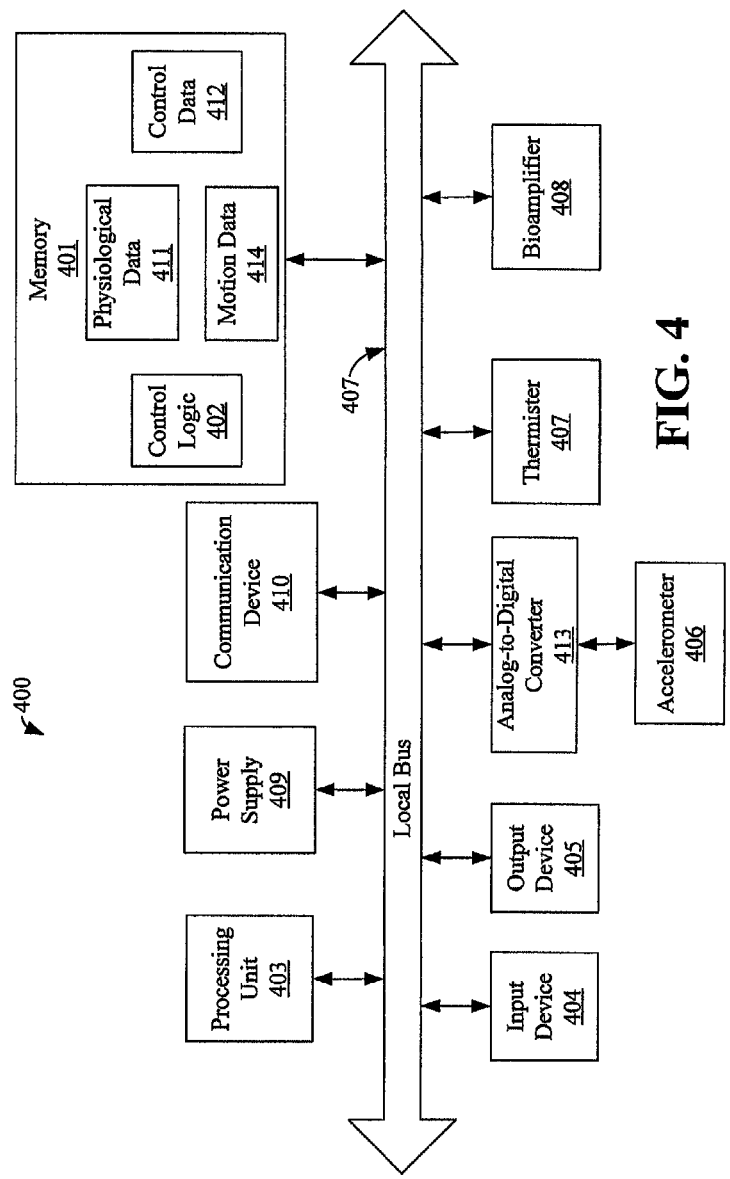
FIG. 4 is a block diagram depicting an exemplary computing system of the wearable health monitoring device as depicted in FIG. 1

During operation, the wearable health monitoring device 100 extracts features specifically related to the user's motion, respiration, cardiac activity, temperature, and the like. In order to extract such features related to motion of the user 301, an accelerometer described further with reference to FIG. 4, is used, which extracts features based upon a 3-axis coordinate system depicted in FIG. 3. Exemplary processes and methods for extracting such features are described further herein, and include processes for estimating the user's level of activity or approximating caloric expenditure, categorizing user activity, detecting a fall, step detection, or orientation detection, for example.

FIG. 4 is a block diagram depicting an exemplary controller 400 of the present disclosure that is contained in the controller housing 103 (FIG. 1) of the wearable health monitor 100 (FIG. 1).

The exemplary controller 400 comprises a processor 403, an output device 405, an input device 404, a communication device 410, and a power supply 409. In addition, the exemplary controller 400 comprises a thermistor 407 and one or more bioamplifiers 408. Each of these components communicates over local interface 407, which can include one or more buses. Furthermore, the controller 400 comprises an accelerometer 406 and an analog-to-digital converter (ADC) 413.

Controller 400 further comprises control logic 402, physiological data 411, motion data 414, and control data 412. Control logic 402 can be software, hardware, or a combination thereof. In the exemplary controller 400 shown in FIG. 4, control logic 402, is shown as software stored in memory 401. Memory 401 may be of any type of memory known in the art, including, but not limited to random access memory (RAM), read-only memory (ROM), flash memory, and the like.

As noted hereinabove, control logic 402, physiological data 411, motion data 414, and control data 412 are shown in FIG. 4 as software stored in memory 401. When stored in memory 401, control logic 402, physiological data 411, motion data 414, and control data 412 can be stored and transported on any computer-readable medium for use by or in connection with an instruction execution system, apparatus, or device, such as a computer-based system, processor-containing system, or other system that can fetch the instructions from the instruction execution system, apparatus, or device and execute the instructions.

In the context of the present disclosure, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium Processor 403 may be a digital signal processor (DSP) or other type of circuitry configured to run the control logic 402 by processing and executing the instructions of the control logic 402.

The communication device 410 may be, for example, a low-powered radio device, e.g., a radio semiconductor, radio frequency antenna (RF antenna); a wired communication device such a RS232, USB, or Ethernet; or other wireless communication device, such as a magnetic communications scheme or infrared scheme; or any type of communication device, which communicatively couples the controller 400 to the data-receiving device 302 (FIG. 3) and/or the central monitoring device 305.

In an embodiment having a data-receiving unit 302, physiological data 411 and motion data 414 can be relayed in a real-time manner, a periodic manner, an "as they occur" fashion, or some combination of the three. For example, a serious condition such as an individual falling could be relayed to the central monitoring device 305 (FIG. 3).

In one embodiment, the bioamplifier 408 is a device that interfaces with the electrodes 200. Thus, the bioamplifier 408 gathers, amplifies, filters and conditions the signal integrity of human physiological activity for use by the control logic 402. The signals (not shown) collected by the bioamplifier 408 from the electrodes 200 relate to the nervous system of the user 301 (FIG. 3). In one embodiment, the signals collected are stored as the physiological data 411, and are used by the control logic 402.

The output device 405 is a device for communicating information to the user 301 (FIG. 3). The output device 405 may be, for example, an LED that indicates that power is on. In addition, the output device 405 may be a speaker that emits a sound upon the occurrence of a particular event, e.g., when the battery needs to be charged or upon activation.

Physiological data 411 includes data obtained from the one or more sensors, e.g., the thermistor 407 or the bioamplifier 408. Hence, the physiological data 411 comprises data indicative of physiological aspects of the user 301 (FIG. 3). Examples of physiological data 411 include data indicative of ECG readings, heartbeat readings, temperature readings, or the like.

Motion data 414 includes data obtained from the accelerometer 406. Hence, the motion data 414 comprises data indicative of movement of the user. In the 3-axis accelerometer embodiment, the motion data 414 includes data indicative of the user 301 in an X-direction, Y-direction, and the Z-direction.

The input device 404 enables the user 301 to enter data into the controller 400. In the exemplary controller 400, the input device 404 is the actuator 102 (FIG. 1). When the actuator is selected, the controller 400 recognizes this as a user button which generates a message which is sent over the network 303 and is detected by the remote device monitor 304. Other input devices may be used in other embodiments. For example, the input device 404 may be a keyboard or a touch screen for performing particular operations on the controller 400.

In one embodiment, the input device 404 is a microphone (not shown), and an exemplary output device 405 is a speaker (not shown), as described hereinabove. In such an embodiment, the speaker and the microphone enable the user 301 to be in communication with the device monitor 304 where the device monitor 304 is a person. In such an example, the wearable health monitoring device 100 detects an event, such as, for example, a fall or a negative change in the user's physiological condition based upon received physiological data 411. The central monitoring device 305 receives the physiological data 411 and alerts the device monitor 304 to the particular concern. The device monitor 304 then contacts the user 301 over the network 303 via the microphone/speaker input/output arrangement.

The thermistor 407 is conductively coupled to the metal contact 207 (FIG. 2) as described hereinabove. The thermistor 407 is a device that measures a skin temperature of the user 301 where the thermistor 407 is in contact with the metal contact 207, which is in contact with the skin of the user 301. In one embodiment, the thermistor 407 is a thermocouple (not shown) integrated with the housing 103, and the thermocouple protrudes from the backside of the housing 103. Placing it on the backside of the control housing 103 places the thermocouple in direct contact with the user's skin. In such an embodiment, leads (not shown) from the thermocouple are attached to the controller 400.

In another embodiment, the metal contact 207 (FIG. 2) is mounted inside the controller housing 103 and is mounted to the thermistor 407 of the controller 400. In such an embodiment, the thermistor 407 is mounted so that either the thermistor 407 is in direct contact with the thermally conductive metal contact 207 integrated with the controller housing 103 for detecting physiological data 411 indicative of skin temperature or it is positioned so that an intermediary thermally conductive material (not shown) can connect to the thermistor 407 and the contact 207. The metal contact 207 may be comprised of materials, such as, copper, aluminum, stainless steel, thermally conductive polymers or plastics. In one embodiment, the metal contact 207 is made of a combination of materials such as a thermally conductive gap filler connecting or thermal grease which connects the thermal contact 207 to the thermistor 407.

In one embodiment, the accelerometer 406 is a 3-axis accelerometer for monitoring motion. The accelerometer 406 may be a direct current ("DC") response or a non-DC response accelerometer. In one embodiment, the accelerometer 406 is a microelectromechanical ("MEMS") piezoresistive technology sensor (not shown), however other types of accelerometers known in the art or future-developed may be used in other embodiments of the controller 400.

In one embodiment, the accelerometer 406 measures acceleration due to gravity and physical movement and transmits the raw analog signals to the ADC 413. The ADC 413 translates the received analog into digital data indicative of the received analog signals (not shown). The ADC 413 provides the digital data indicative of the analog signals to the control logic 402, which can store the digital data as motion data 414. The control logic 402 then calculates and stores additional motion data 414 including activity-induced energy expenditure (AEE) and/or orientation, based upon the motion data 414. In addition, the control logic 402 can use the motion data 414 to detect a fall, detect steps made by the user 301, and categorize activity performed by the user 301.

The accelerometer 406 may be a single (or dual) axis accelerometer arranged to create a three-axis orthogonal coordinate system, as depicted in FIG. 3 as X, Y, and Z axes. FIG. 3 illustrates one possible axis orientation for a wearable health monitoring device including a 3-axis accelerometer sensor.

During extraction of the physiological data 411 and motion data 414, the control logic 402 reacts quickly to changes in real-time and also reduces the data stream, thereby maximizing the storage capabilities of memory 401. Reducing the data stream may refer to techniques for averaging the data, or inspecting the real-time stream for certain feature extraction. One such technique is described in U.S. patent application Ser. No. 11/972,335 entitled Wireless Sensor Network Context Data Delivery System and Method.

Figure 5:
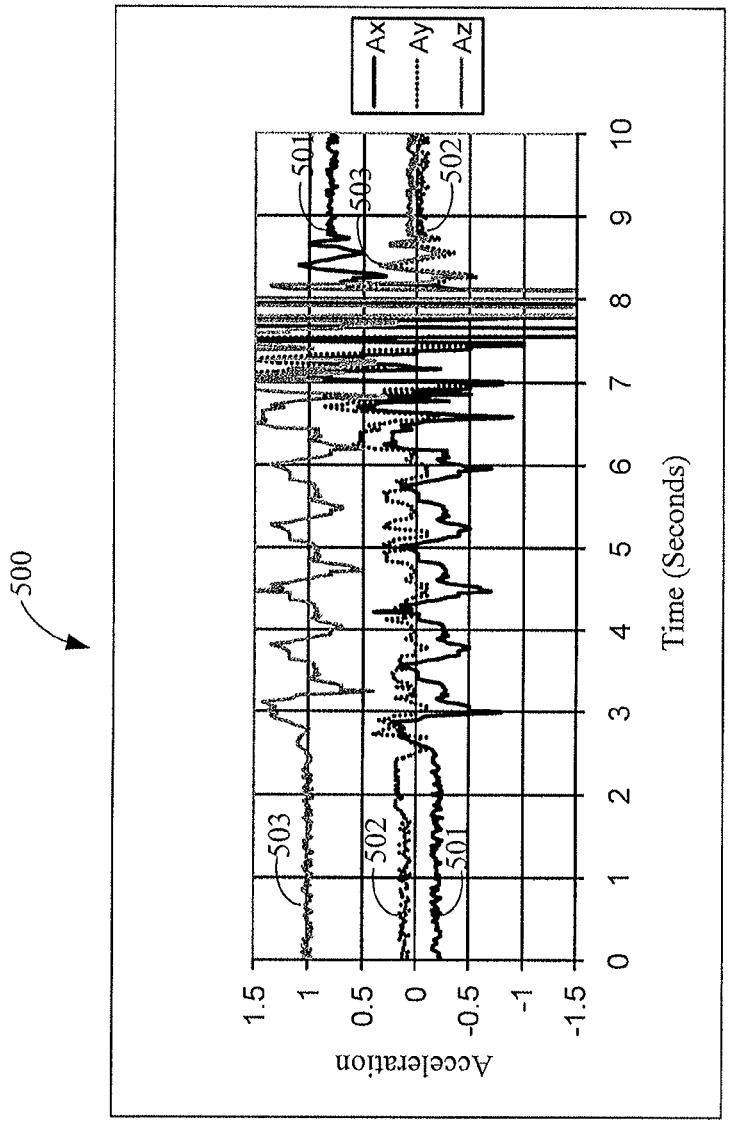
FIG. 5 is a graph depicting a plurality of outputs of a 3-axis accelerometer depicting a human standing, walking, and falling.

FIG. 5 is a graph 500 that illustrates digitized signals 501-503 obtained from an accelerometer 406 (FIG. 4) wherein the accelerometer 406 is a 3-axis accelerometer. As described herein, the accelerometer 406 provides the raw analog signals to the ADC 413 before the signals 501-503 are provided to the control logic 402.

The accelerometer 406 and ADC 413 from which the data plotted in the graph 500 is obtained, is housed in the controller housing 103 (FIG. 1) by the user 301 (FIG. 3) in the upper torso position depicted in FIG. 3. As shown in FIG. 3, three axes, i.e., X-axis, Y-axis, and Z-axis, denote the three dimensions of movement possible for the user 301 and for which the accelerometer 406 obtains signals.

The graph 500 comprises an "Acceleration" axis in "g" and a corresponding "Time" axis in seconds. Note that the symbol "g" refers to the gravitational pull of Earth at sea level. In addition, the graph 500 comprises the signal 501, the signal 502, and the signal 503, which correspond to the X-axis, the Y-axis, and the Z-axis of FIG. 3. Thus, the signal 501 corresponds to movement of the user 301 in an X-direction, the signal 502 corresponds to movement of the user 301 in a Y-direction, and the signal 503 corresponds to movement of the user 301 in a Z-direction. Each signal is indicated in the legend as Ax, Ay, and Az, respectively.

The graph 500 depicts approximately two seconds of idle standing, from Time=0 seconds to Time=2 seconds. Further, the peaks indicated in each notation 501-503 from approximately Time=3 seconds to Time=7 seconds represent approximately four seconds of walking (six discrete steps depicted) followed by a fall at approximately Time=8 seconds. The fall lasts approximately two seconds from Time=7 seconds to Time=9 seconds, followed by a change in orientation and a period of inactivity after Time=9 seconds.

The change in orientation is indicated by the change in location on the acceleration axis of the signals 501-503 following the fall. Note that this orientation is calculated as a function of the static response due to gravity and how it acts on each axis. Hence, after the indicated fall, the signal 501 in the X-direction changes from approximately 0 g prior to the fall to approximately Acceleration=1 g after the fall. The signal 502 in the Y-direction remains very near its original value, and the signal 503 in the Z-direction changes from approximately 1 g prior to the fall to slightly less than 0 g after the fall. The change in the DC components of the acceleration values indicates a change in orientation. As an example, prior to the fall, the user 301 may have been in an upright position; however, after the fall, the user may now be in a supine position.

Furthermore, the notations 501-503 level at around Time=9 seconds, and the signals 501-503 do not exhibit any steeply graduated peaks in the acceleration. This leveling out after the fall, i.e., after Time=9 seconds, indicates a period of inactivity.

Figure 6:
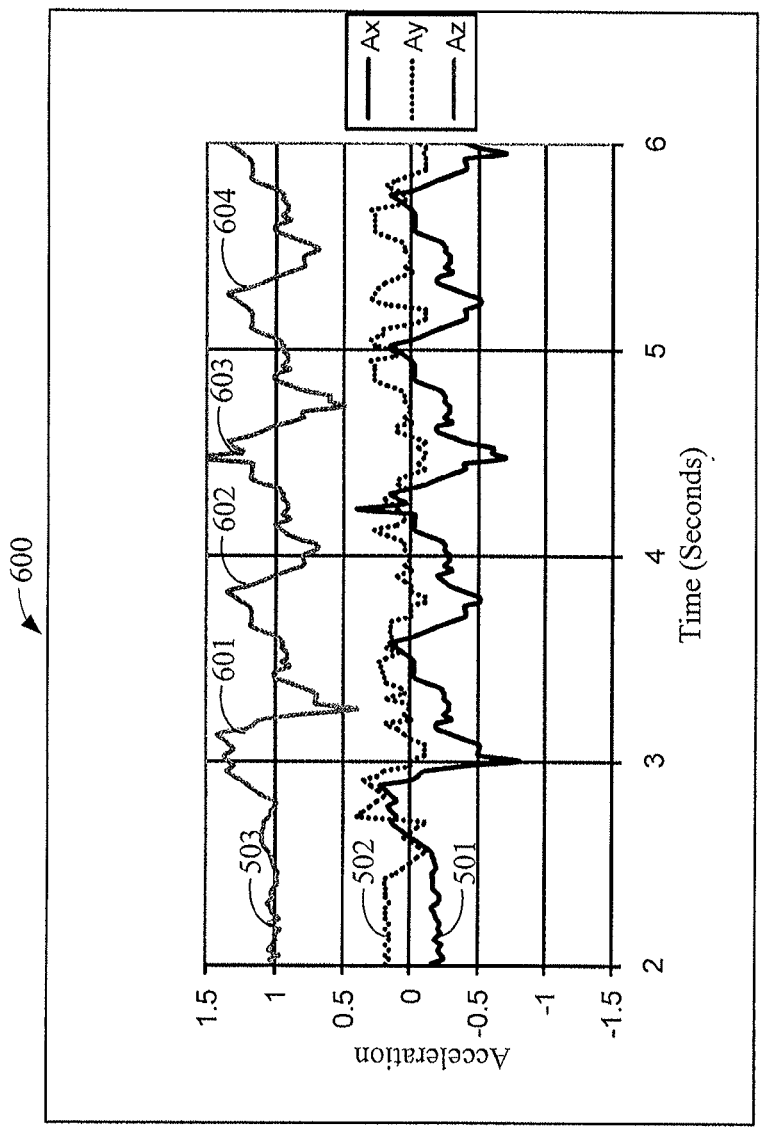
FIG. 6 is a graph depicting a portion of the graph depicted in FIG. 5 from time=2 seconds to time=6 seconds.

FIG. 6 is a graph 600 that illustrates in more detail the movement of the user 300 (FIG. 3) from Time=2 seconds to Time=6 seconds in the graph 500 of FIG. 5. Note that the notations of the signals 501-503 remain the same, i.e., signal 501 is indicative of movement in the X-direction, signal 502 is indicative of movement in the Y-direction, and signal 503 is indicative of movement in the Z-direction.

The four-second period from Time=2 to Time=6 seconds encompasses approximately four steps (walking), and the steps are indicated by the peaks 601-604 in the Z-direction represented by signal 503. Each signal 501-503 comprises peaks; however, for simplicity and brevity only those peaks in the Z-direction are identified in FIG. 6.

Figure 7:
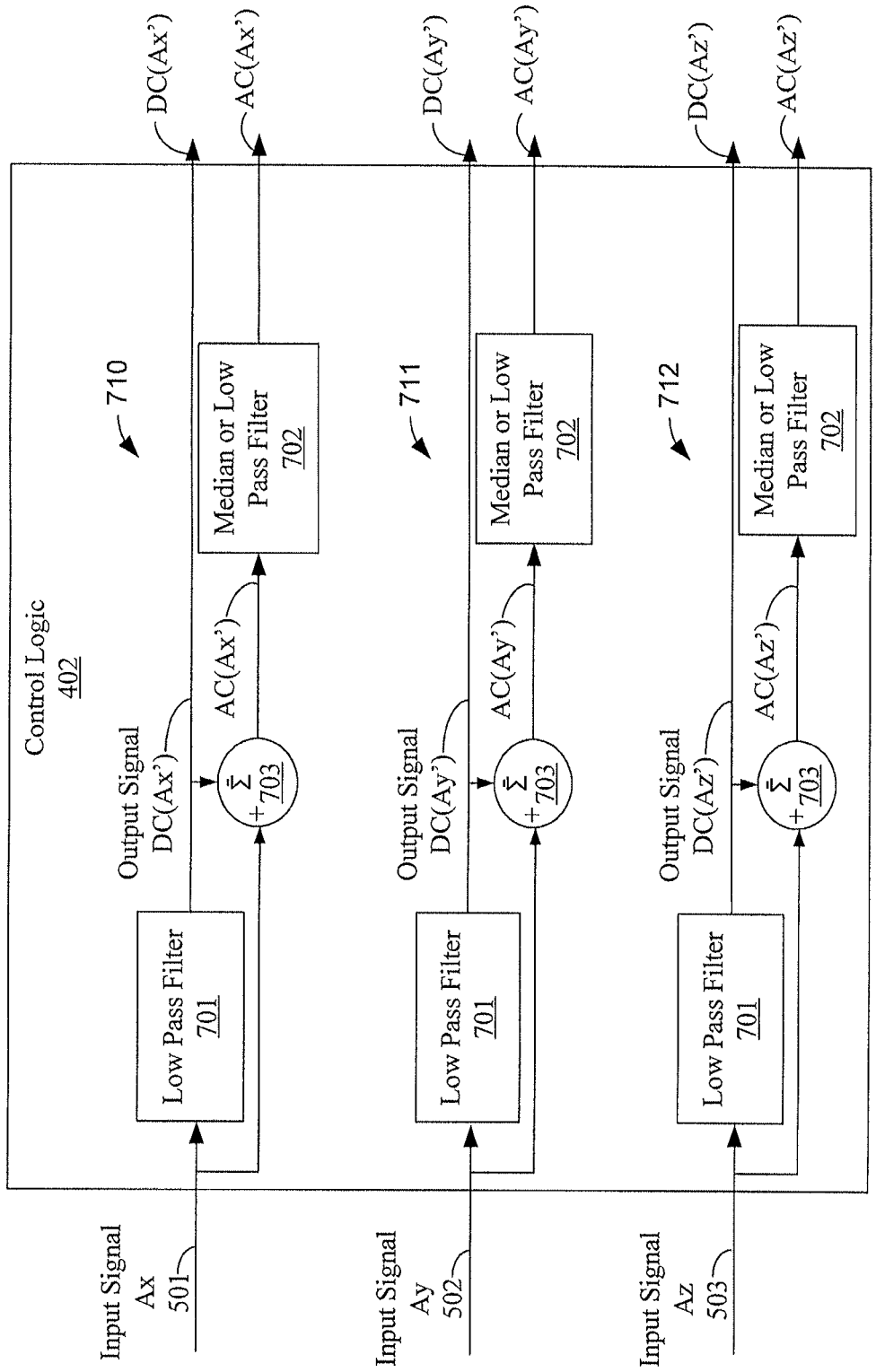
FIG. 7 is a block diagram depicting exemplary architecture of the control logic of the health monitoring device depicted in FIG. 4.

Additionally, there is a DC offset to each signal 501-503, and in particular, there is an offset in the Z-direction represented by signal 501 of 1 g. As indicated hereinabove with reference to FIG. 3, when the user 301 is in an upright position, the Z-direction is most affected, relative to the other directions, by the static effects of gravity or acceleration in g. Thus, the offset of 1 g with respect to the Z-direction is greater than that in the X-direction and Y-direction, i.e., approximately 0 g in both cases. FIG. 7 depicts exemplary architecture and functionality of the control logic 402 (FIG. 4) in accordance with an embodiment of the present disclosure. Note that the control logic 402 can be software, hardware, or any combination thereof.

As described with reference to FIGS. 4-6, the accelerometer 406, assumed for purposes of illustration to be a 3-axis accelerometer, transmits raw analog signals (not shown) detected by a respective sensor (not shown) of the accelerometer 406 corresponding to each of the X, Y, and Z directions, to the ADC 413 (FIG. 4). The ADC 413 translates the analog signals received into digital signals Ax, Ay, and Az 503, and provides the signals to the control logic 402. Note that each of these signals 501-503 comprises an alternating current (AC) component and direct current (DC) component. The ADC 413 then provides the digitized signals 501-503 to the control logic 402.

FIG. 7 depicts an exemplary embodiment of control logic 402. In this regard, the control logic 402 comprises three separate tiers 710-712 that operate to manipulate each of the three separate input signals Ax 501, Ay 402, and Az 503 provided by the ADC 413 (FIG. 4) into data indicative of an AC component, i.e., AC(Ax'), AC(Ay'), and AC(Az'), and data indicative of a DC component, i.e., DC(Ax'), DC(Ay'), and DC(Az').

The circuits 710, 711, and 712 comprise low pass filters 701. The low pass filters 701 remove high-frequency noise (not shown) of the input signal Ax 510, and Ax 503 and transmits as output the direct current (DC) portion of each of the signals DC(Ax'), DC(Ay'), and DC(Az').

In addition, the signals Ax, Ay, and Az are transmitted to summation circuits 703. The summation circuits 703 further receive the output signals DC(Ax'), DC(Ay'), and DC(Az') from the low pass filter 701. The summation circuit 703 subtract the output signals DC(Ax'), DC(Ay'), and DC(Ax') from the signals Ax, Ay, and Az to obtain the AC components AC(Ax'), AC(Ay'), and AC(Az') of the signals Ax, Ay, and Az, respectively. Finally a post filter median or low pass filter is applied to further smooth the signals AC(Ax'), AC(Ay'), and AC(Az').

When implemented in firmware or software and stored in memory 401 (FIG. 4), the motion data 414 (FIG. 4) indicative of the input signals Ax, Ay, and Az obtained from the accelerometer 406 are represented as a stream of discrete samples occurring in real-time, as defined by an application sampling frequency, the graphs of which are illustrated in FIGS. 5 and 6.

Figure 8:
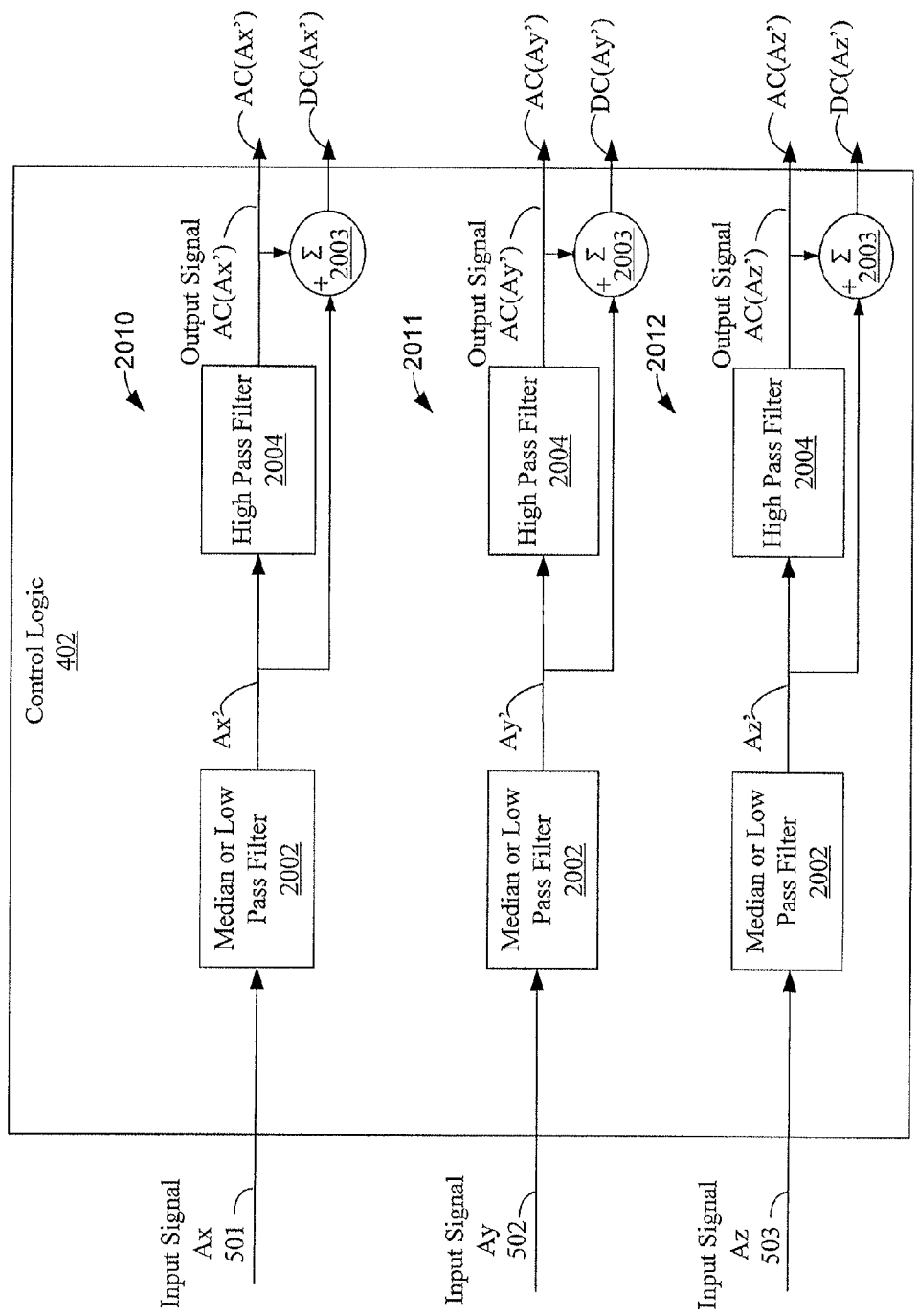
FIG. 8 is a block diagram depicting another exemplary architecture of the control logic of the health monitoring device depicted in FIG. 4.

FIG. 8 depicts another exemplary architecture and functionality of the control logic 402 (FIG. 4) in accordance with an embodiment of the present disclosure. Note that the control logic 402 can be software, hardware, or any combination thereof.

As described hereinabove, the ADC 413 translates the analog signals received into digital signals Ax 501, Ay 502, and Az 503, and provides the signals to the control logic 402. Note that each of these signals 501-503 comprises an alternating current (AC) component and direct current (DC) component. The ADC 413 then provides the digitized signals 501-503 to the control logic 402.

The control logic 402 depicted in FIG. 8 comprises three separate tiers 2010-2012 that operate to manipulate each of the three separate input signals Ax 501, Ay 502, and Az 503 provided by the ADC 413 (FIG. 4) into data indicative of an AC component, i.e., AC(AX'), AC(Ay'), and AC(Az'), and data indicative of a DC component, i.e., DC(Ax'), DC(Ay'), and DC(Az').

The circuit 2010 comprises a median or low pass filter 2002 with a very low cutoff frequency. In an exemplary embodiment, this is set at 0.1 Hz. The filter 2002 is used to remove high-frequency noise of from the signal Ax to obtain resultant signal Ax'. The signal AX' is then transmitted through a high pass filter 2004 to generate the alternating current portion AC(Ax') only of the Ax' signal.

In addition, the signal Ax' is transmitted to a summation circuit 2003, and the summation circuit 2003 also receives the signal AC(Ax') from the high pass filter 2004. The summation circuit 2004 subtracts AC(Ax') from the input signal Ax'to obtain the DC component DC(Ax') of the signal Ax. Note that in the embodiment shown in FIG. 8, a median filter can be applied to post filter and further smooth the AC(Ax') signal.

It is understood that there exists additional variations of this architecture and functionality that result in similar intermediate signals. For example, one embodiment employs DC extraction using a low pass filter to achieve the DC component and subtracting the DC component from the input signal to obtain the AC signal component, as is shown in FIG. 7, while in another embodiment, employs AC extraction using a high pass filter to obtain the AC component and subtracting the AC component from the input signal to obtain the DC signal component, as shown in FIG. 8.

With reference to FIG. 4, the motion data 414 comprises data indicative of a plurality of AC signals AC(Ax'), AC($A_y$'), and AC($A_z$') and a plurality of DC signals DC signals DC(Ax'), DC($A_y$'), and DC($A_z$'). In order to calculate activity-induced energy expenditure (AEE), the control logic 402 receives the plurality of generated signals AC($A_x$'), AC($A_y$'), and AC($A_z$') from the motion data 414 or from the ADC 413, as described hereinabove. The control logic 402, upon receipt of the signals AC($A_x$'), AC($A_y$'), and AC($A_z$'), calculates AEE based upon the following formula:

$$AEE = \int_{t}^{t+T} \sqrt{AC(A_x')^2 + AC(A_y')^2 + AC(A_z')^2}, \quad \text{A.1}$$

where T is the integration period.

Note that an integration period in formula A.1 is application dependent. In one embodiment, the integration period t to (t+T) is one minute, i.e., T=60 seconds. The calculated AEE is useful for interpreting the magnitude of a response. For exemplary purposes of algorithms and methods employed by control logic 402, AEE is of the order of approximately one second in period (T=1 second).

In one embodiment, the control logic 402 implements the integral from discrete samples of the signals AC($A_x$'), AC($A_y$'), and AC($A_z$') stored as motion data 414 by calculating a cumulative sum of the samples. As an example, for each T/f, discrete sample (where $f_s$ represents the application sampling frequency), the control logic 402 calculates the square root of AC($A_x$')$^2$+AC($A_y$')$^2$+AC($A_z$')$^2$ The sum of these values represents an AEE for a given time, T. When the signals are processed in real-time, a temporary variable is first initialized to zero (every T/$f_s$ operations) and a cumulative sum is generated. The AEE result is available every T/$f_s$ operations.

Figure 9:
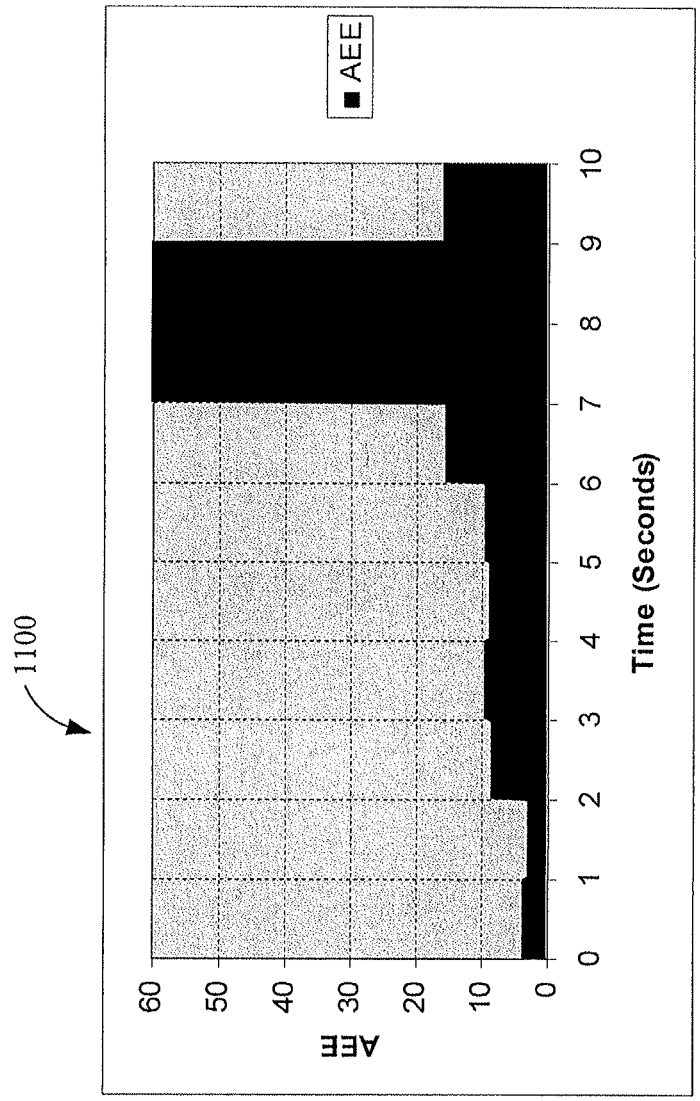
FIG. 9 is a bar chart depicting exemplary activity-induced energy expenditure.

As an example, FIG. 9 shows AEE for a one second integration periods as calculated over an entire ten second time interval. Each second the control logic 402 performs the squared summation provided for in formula A.1, and the graph 1100 is a bar graph showing the magnitudes of the AEE over the ten second time interval.

In addition to calculating AEE, the control logic calculates an orientation of the user 301 (FIG. 3) based upon the DC signals DC(Ax'), DC(Ay'), and DC(Az') stored as motion data 414. For the purpose of the present disclosure, orientation of the user 301 refers to whether the individual's upper torso region is horizontal or vertical.

Orientation

Figure 11:
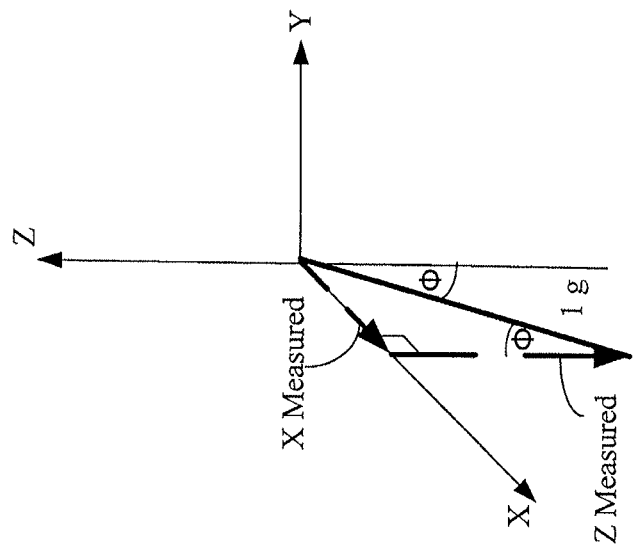
FIG. 11 is a diagram depicting the resultant effect of the gravity vector on the 3-axis coordinate depicted in FIG. 10.
Figure 10:
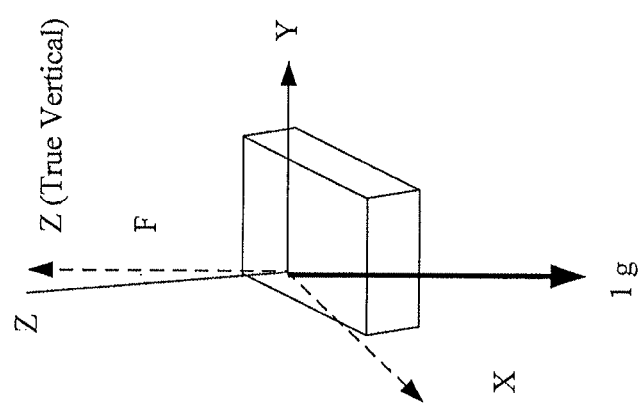
FIG. 10 is a diagram depicting a 3-axis coordinate and a gravity vector.
Figure 13:
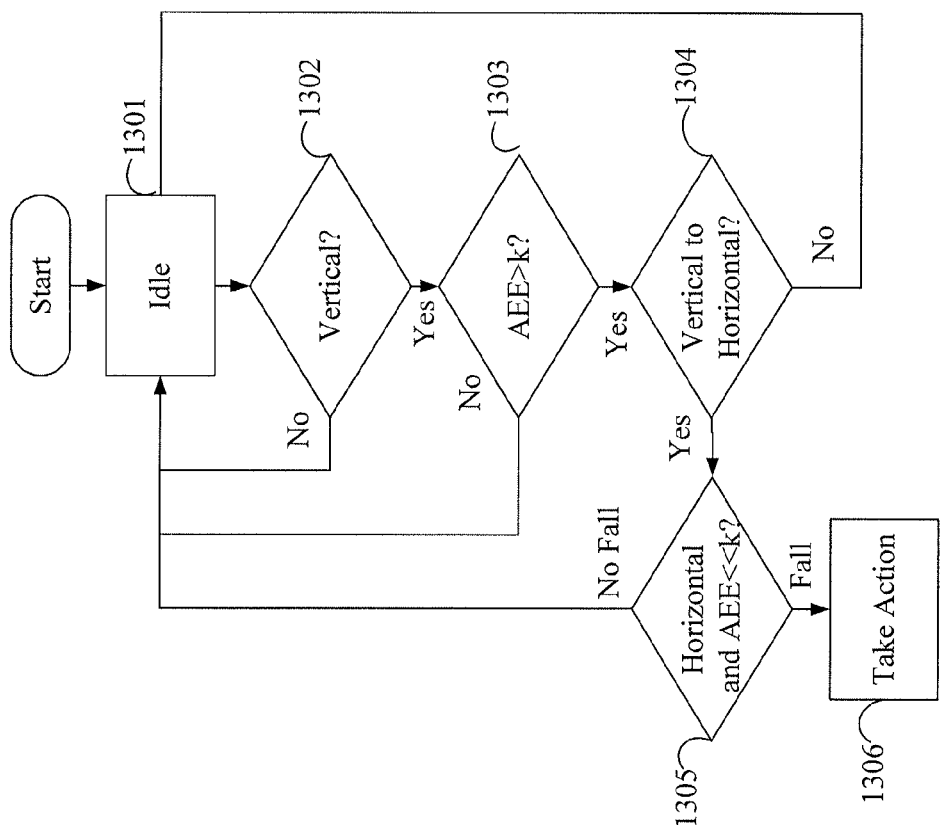
FIG. 13 is a flowchart depicting exemplary architecture and functionality of the control logic depicted in FIG. 4 for determining whether a user of the health monitoring device depicted in FIG. 1 has fallen.

With reference to FIGS. 10 and 11, the control logic 402 receives and analyzes the signals DC($A_x$'), DC($A_y$') and DC($A_z$') to determine an angle Φ between the z-dimension axis and the effect of gravity represented by the vector "1 g." FIG. 11 depicts the static effects of gravity and how the vector "1 g" is measured on each axis X, Y, and Z. FIG. 13 shows the effect of gravity on each axis prior to a fall, where the user was in the vertical orientation and just after a fall, where the user was in a horizontal orientation.

The present disclosure discloses a method for calculating this angle Φ as a function of DC($A_x$'), DC($A_y$'), and DC($A_z$'). The angle between any two vectors can be determined by taking the dot product:

$$u \cdot v = |u||v| \cos \phi$$

Let u be the ideal unit vector experienced if the accelerometer was completely vertical and gravity acted in 1 g in the z-axis. Then, $$u=(0,0,1)$$

And let v be the vector experienced in the current orientation:

$$v=DC(x'),DC(y'),DC(z')$$

Then the angle Φ is calculated as follows:

$$\phi = \cos^{-1}\left(\frac{u \cdot v}{|u||v|}\right) = \frac{1 \times DC(z')}{1 \times \sqrt{DC(x')^2 + DC(y')^2 + DC(z')^2}}$$

One embodiment of the present disclosure categorizes horizontal and vertical orientation in terms of Φ as follows:

| Angle Φ | Orientation |
|---|---|
| Φ < β or Φ > γ | Vertical |
| B < Φ < γ | Horizontal |

Where 0° < β < 90° and 90° < γ < 180°

Yet another embodiment simplifies the calculation by recognizing that the angle Φ is a function only of $DC(A_z')$ and the magnitude of the vector formed by gravity. Because the magnitude of the measured vector should be very near 1 g, it can be approximated—thus avoiding the inverse cosine calculation—by forming a look-up table or simple comparison based on $DC(A_z')$. The following table illustrates one possible method:

| DC(z') | Orientation |
|---|---|
| DC(z') > $k_{h1}$ or DC(z') < $k_{h2}$ | Vertical |
| $k_{h1}$ > DC(z') > $k_{h2}$ | Horizontal |

Where cos(0°) > $k_{h1}$ > cos(90°) and cos(90°) > $k_{h2}$ > cos(180°)

Yet another embodiment first compensates for offset from the initial device placement as described within "Wireless Sensor Network System And Method For Using The Same", U.S. Provisional Patent Application No. 60/884,352, filed Jan. 10, 2007. Using the methods contained within combined with those disclosed in this present disclosure, it is possible to extract orientation even when the device is erroneously worn—such as if it were placed upside down.

Step Detection

In addition to calculating orientation and AEE, the control logic 402 further detects steps performed by the user 300 (FIG. 3) as described with reference to FIG. 12. In order to determine whether a step has occurred by the user 300, the control logic continuously monitors the signals $AC(A_x')$, $AC(A_y')$, and $AC(A_z')$.

Figure 12:
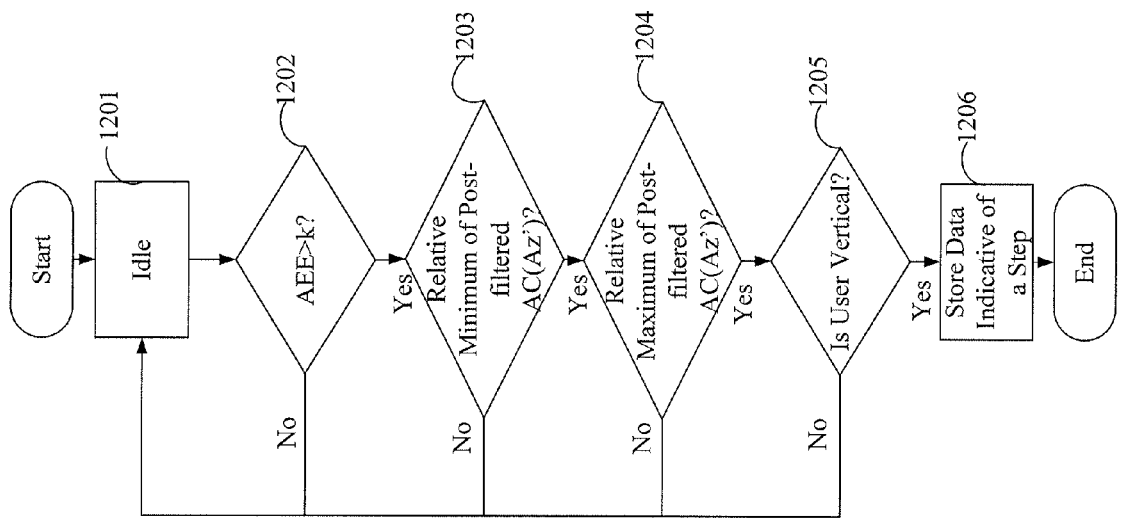
FIG. 12 is a flowchart depicting exemplary architecture and functionality of the control logic depicted in FIG. 4 for determining whether a user of the health monitoring device depicted in FIG. 1 has taken a step

FIG. 12 is a flowchart depicting exemplary architecture and functionality of the control logic 402 for detecting a step of a user 301 (FIG. 3). The control logic 402 initially remains idle, as indicated by step 1201 until a minimum amount of activity energy estimation (AEE) has met or exceeded a threshold "K," as indicated in step 1202.

A step is determined by detecting a relative minimum followed by a relative minimum on the post filtered AC(Az') signal within a given time window and further qualifying by assuring the user is not in a supine position (using intermediate signal orientation).

Next the control logic 402 determines whether there has been a relative minimum of the post-filtered AC(Az') as indicated in step 1203. In one embodiment, the control logic 402 detects the relative minimum from the signal AC(Az') by comparing each digital sample in $AC(A_z')$ to one or more previous and subsequent samples in AC(Az'). Thus, a relative minimum is detected when the current discrete sample is less than the previous sample and the following sample is greater than the current sample.

If there is not a relative minimum in step 1203, the control logic 402 remains idle; however, if there is a relative minimum, the control logic 402 determines whether there is a relative maximum from signal $AC(A_z')$ in step 1204. Similar to the discussion with reference to step 1203, the control logic 402 detects the relative maximum from the signal AC(Az') by comparing each digital sample in $AC(A_z')$ to one or more previous and subsequent samples in AC(Az'). Thus, a relative maximum is detected when the current discrete sample is greater than the previous sample and the following sample is less than the current sample.

If there is not a relative maximum in step 1204, the control logic 402 remains idle; however, if there is a relative maximum, the control logic 402 determines if the user is in a non-horizontal orientation, as indicated in step 1205.

Having satisfied the sequence of events identified in steps 1201-1205, the control logic 402 stores motion data 414 indicative of a step having been performed at the particular time, as indicated in step 1206. If the precise time occurrence of the step is of importance to the application, this can be defined by the user and stored as control data 412.

In another embodiment, the magnitude of the relative maximum and relative minimum can be used to further qualify the step detection. In yet another embodiment, the phase relationship between other axes could be examined to further qualify the step.

In one embodiment of the present disclosure, the control logic 402 monitors the number of steps taken by the user 301 over time. In this regard, the control logic 402 can start a counter and each time a step is detected and stored in step 1206, the counter can be incremented. After a given time interval, for example sixty seconds, the control logic 402 can stop the counter and store motion data 414 (FIG. 4) in memory 401 (FIG. 4) indicating the number of steps taken during the time interval. The control logic 402 can transmit this motion data 414 to the central monitoring device 305 for storage, display, or further analysis.

Fall Detection

FIG. 13 is a flowchart illustrating exemplary architecture and functionality of the control logic 402 for detecting a fall of the user 301 in accordance with an embodiment of the present disclosure.

As described hereinabove, control logic 402 remains in an idle state, as indicated in step 1301. The control logic 402 determines if the user 301 is in a vertical position, as indicated in step 1302. If the user is in a vertical position, then the control logic 402 compares a calculated AEE with a predefined threshold "k," as indicated in step 1303. The threshold k is set sufficiently high so as not to be exceeded by normal activity levels. In another embodiment, AEE is sampled more often and AEE threshold exceeding can be determining if n out of m consecutive AEE samples are above k. In yet another embodiment, this can be further qualified to ensure that at least one of the m sampled AEE values is above a higher threshold j, where j>k.

The control logic 402 then determines whether there is a change in orientation from vertical to horizontal, as indicated in step 1304. If a continued horizontal state with relatively low activity (AEE<1 and 1<<k) for some period of time, as indicated in step 1305, the control logic 402 takes action, in step 1306, e.g., stores data indicative of a fall or alerts the central monitoring device 305.

If while in steps 1301-1304, an event does not transpire in a reasonable elapsed time, the control logic 402 returns to the idle (appropriate orientation) state in step 1301.

Figure 14:
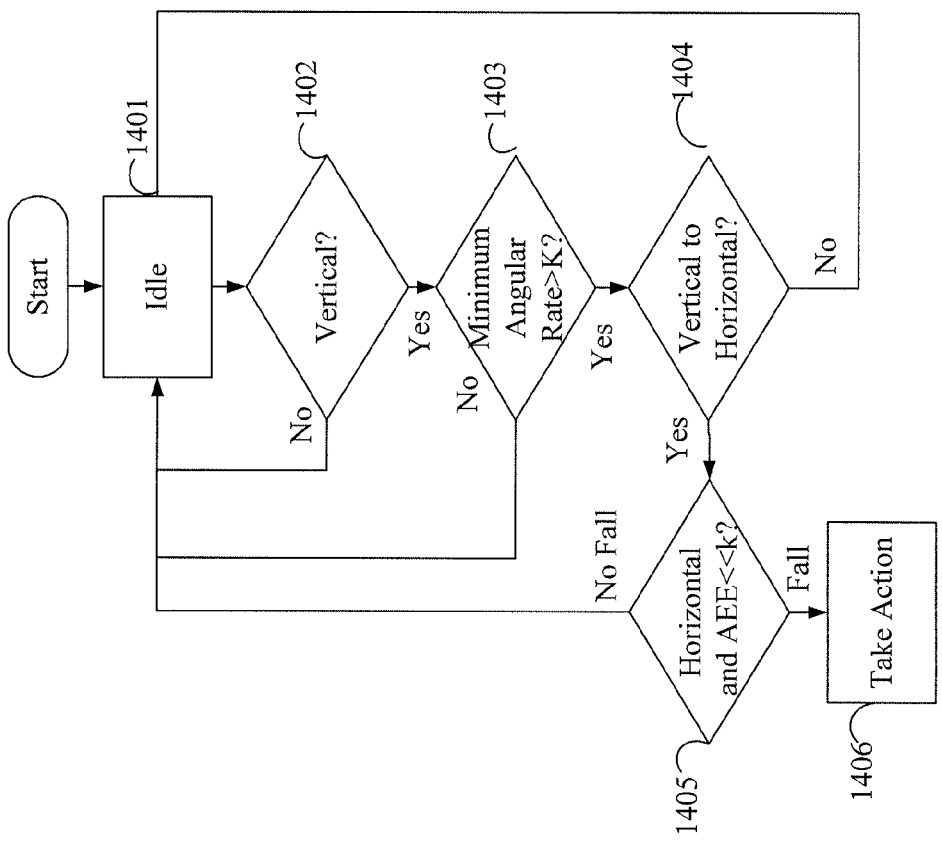
FIG. 14 is a flowchart depicting another exemplary architecture and functionality of the control logic depicted in FIG. 4 for determining whether a user of the health monitoring device depicted in FIG. 1 has fallen.

FIG. 14 depicts additional architecture and functionality of the control logic 402 for determining a fall. In step 1401, the control logic 402 remains idle, until the control logic 402 determines whether the user 301 (FIG. 3) is vertical, in step 1402.

In step 1404, the control logic 402 determines whether there is a change in orientation from vertical to horizontal. If the control logic 402 determines that the user 301 is in a continued horizontal state with relatively low activity (AEE<l) for some period of time, as indicated in step 1405, the control logic 402 takes action in step 1406. In this regard, the control logic 402 may store data indicative of a fall or the control logic 402 may transmit an alert to central monitoring device 305 (FIG. 3).

Category of Activity

In one embodiment of the present disclosure, the control logic 402 categorizes activity of the user 301 based upon data received. The present disclosure discloses a method for categorizing user activity. Using a microcontroller or DSP and having employed the signal processing architecture disclosed in present disclosure, derived signals Orientation, AEE, and Steps are of interest. The method provides for discerning four categories of activity: sleeping, sitting or standing, walking, and running.

The table below defines these categories of activity in terms of orientation, AEE, and whether or not steps are being detected.

| Orientation | AEE | Steps Detected | Category of Activity |
|---|---|---|---|
| Horizontal | AEE < k | — | Resting[1] |
| Vertical | — | No | Standing or Sitting |
| Vertical | l < AEE < m | Yes | Walking |
| Vertical | AEE > m | Yes | Vigorous Walking or Running |

Where $k \ll l \ll m$

Although not explicitly depicted in the above table, the present disclosure also discloses monitoring of other physiological signals if available. For example, while the user is horizontal, it is imperative to ensure that the individual is okay. Heart rate, if available, provides a good indication of this and can be used to differentiate sleeping and other life threatening situations. In addition, the above table does not accommodate history and in the case of a user having suffered a fall, software should keep state of this and use it to qualify the categorized activity. That is, a user is only sleeping if having not suffered a fall and all vitals are still okay. In addition, all extracted features should be qualified with whether the device is being worn. A method for determining if the device is being worn is disclosed within the present disclosure.

The present disclosure discloses a method for discerning periods of sleep and wake. For present purposes, sleep and wake are more simply categorized by sleep and not sleep. Based on the methods for categorizing activity which has already been disclosed, it becomes possible to recognize periods of rest and consequently periods of non-rest. For most purposes, rest and sleep are synonymous.

One embodiment, however, makes use one or more of heart rate, respiration, and skin temperature sensors when available. In general, heart rate, respiration rate, and skin temperature decline while sleeping. Under such embodiments, the present disclosure discloses a method for discerning rest from sleep by recording these parameters at onset of rest. If the parameters fall below a certain threshold (relative to recorded parameter at onset of rest), then the activity can be categorized as sleep.

Device Removal

In one embodiment of the present disclosure, the control logic 402 detects whether the device 100 has been removed. Notably, when dry electrodes 200 (FIG. 2) and a metal electrode 207 (FIG. 2) are used, heart beat detection stops and the detected temperature begins to drop quickly if the device 100 is removed from the user 300. In this regard, device removal can be defined as no heart beat and temperature below a threshold. At the beginning of onset of absence of heart beats, the rate of change of temperature must also be used as a determination.

In another embodiment, the control logic 402 uses the electrodes 200 and applies a small potential to the body. By measuring the induced current, it can be determined if the electrodes 200 are in contact with the user's body. If current is induced, the electrodes 200 are in contact with a conductive body and can be determined to be being worn. This can be accomplished by providing a voltage source with a known impedance (a voltage follower amplifier in series with a resistor) and measuring the voltage on the output of the voltage source. If the measured voltage is at or near the source voltage, the loop is open and not in contact with skin. If the measured voltage is significantly lower than the source voltage, then it can be determined that the loop is closed and current is flowing thus causing a voltage drop in the resistive output of the voltage source. It can then be inferred that the electrodes are in contact with a conductive material (presumably human skin). If deemed necessary, this could be further qualified for known resistive properties for humans so as to differentiate from a scenario where the device was laid on another non-human conductive surface.

This disclosure may be provided in other specific forms and embodiments without departing from the essential characteristics as described herein. The embodiments described above are to be considered in all aspects as illustrative only and not restrictive in any manner.

As described above and shown in the associated drawings, the present disclosure comprises a wearable health monitoring device and methods for motion-based feature extraction. While particular embodiments of the disclosure have been described, it will be understood, however, that the disclosure is not limited thereto, since modifications may be made by those skilled in the art, particularly in light of the foregoing teachings. It is, therefore, contemplated by the appended claims to cover any such modifications that incorporate those features or those improvements that embody the spirit and scope of the present disclosure.

What is claimed is:

1. A step detection device configured for detecting a step of a user, comprising:
an accelerometer configured to be coupled to the user's torso and further configured for continuously measuring movement of the user and outputting three signals indicative of the movements of the user in three orthogonal axes, wherein each signal comprises an alternating current (AC) component representing dynamic motion and a direct current (DC) component representing static effects due to gravity; and
a processor electrically coupled to the accelerometer and configured for periodically sampling the three signals and storing digital data indicative of the three signals in a memory, wherein the memory is electrically coupled to the processor, the processor further configured for calculating activity induced energy expenditure (AEE) values based upon the AC components of the sampled signals and wherein AEE is a function of the AC components calculated over an integration period, the processor further configured to determine that the user has taken a step when:
(a) the processor determines when one of the AEE values calculated from the AC components exceeded a first threshold, wherein the first threshold is of a magnitude that indicates activity levels that are above stationary activity levels,
(b) after the processor determines that one of the AEE values has exceeded the first threshold, the processor compares a series of consecutive AC components following the AC component of the AEE value that exceeded the threshold to determine when one of the consecutive AC components has a value less than the other consecutive AC components,
(c) after the processor determines that one of the consecutive AC components has a value less than the other consecutive AC components, the processor determines when one of the consecutive AC components has a value greater than the other consecutive AC components,
(d) after the processor determines when one of the consecutive AC components has a value greater than the other consecutive AC components, the processor determines whether the user is vertical, and
(e) when the processor determines the user is vertical, the processor stores data in the memory indicative of a step,
the processor further configured to transmit the data indicative of the step to a central monitoring device automatically or in response to user input, and the central monitoring device is configured to provide the data indicative of the step to a service provider such that the service provider may determine the user's well-being.

2. The step detection device configured to detect a step of the user of claim 1, wherein the processor is further configured for filtering the AC component from each of the three signals indicative of movement of the user and outputting the respective DC component of each of the three signals indicative of movement of the user for further processing.

3. The step detection device configured to detect a step of the user of claim 2, wherein the processor is further configured for subtracting each of the DC components from a respective one of the signals indicative of movement of the user and outputting the respective AC component of each of the three signals indicative of movement of the user for further processing.

4. The step detection device configured to detect a step of the user of claim 1, wherein the processor is further configured for filtering the DC component from each of the three signals indicative of movement of the user and outputting the respective AC component of each of the three signals indicative of movement of the user for further processing.

5. The step detection device configured to detect a step of the user of claim 4, wherein the processor is further configured for subtracting each of the AC components from a respective one of the signals indicative of movement of the user and outputting the DC component of each of the three signals indicative of movement of the user for further processing.

6. The step detection device configured to detect a step of the user of claim 1, wherein the processor is further configured for calculating the AEE over the integration period by:
(1) calculating the square root of the sum of the squares of the AC components for each discrete sample during the integration period; and
(2) summing the calculated values for each discrete sample during the integration period, wherein the sum is the AEE.

7. A step detection method for detecting a step of a user, comprising:
measuring movement of the user with an accelerometer configured for coupling to a user's torso;
outputting, by the accelerometer, three signals indicative of the movement of the user's torso in three orthogonal axes, wherein each signal comprises an alternating current (AC) component representing dynamic motion and a direct current (DC) component representing static effects due to gravity;
periodically sampling the three signals with a processor coupled to the accelerometer;
storing, by the processor, digital data indicative of the sampled signals in a memory, wherein the memory is electrically coupled to the processor;
periodically calculating, by the processor, activity-induced energy expenditure (AEE) values based on the AC components of the sampled signals and wherein AEE is a function of the AC components calculated over an integration period;
determining, by the processor, that the user has taken a step when:
(a) the processor determines when one of the AEE values calculated from the AC components exceeded a first threshold, wherein the first threshold is of a magnitude that indicates activity levels that are above stationary activity levels,
(b) after the processor determines that one of the AEE values has exceeded the first threshold, the processor compares a series of consecutive AC components following the AC component of the AEE value that exceeded the threshold to determine when one of the consecutive AC components has a value less than the other consecutive AC components,
(c) after the processor determines that one of the consecutive AC components has a value less than the other consecutive AC components, the processor determines when one of the consecutive AC components has a value greater than the other consecutive AC components,
(d) after the processor determines when one of the consecutive AC components has a value greater than the other consecutive AC components, the processor determines whether the user is vertical, and
(e) when the processor determines the user is vertical, the processor stores data in the memory indicative of a step,
transmitting the data to a central monitoring device automatically or in response to user input; and
providing the data, by the central monitoring device, to a service provider for use in determining the user's well-being.

8. The step detection method configured to detect a step of the user of claim 7, further comprising:
filtering, by the processor, the AC component from each of the three signals indicative of movement of the user; and
outputting, by the processor, the DC component of each of the three signals indicative of movement of the user for further processing.

9. The step detection method configured to detect a step of the user of claim 8, further comprising:
subtracting, by the processor, each of the DC components from a respective one of the signals indicative of movement of the user; and
outputting, by the processor, the AC components of the three signals indicative of movement of the user for further processing.

10. The step detection method configured to detect a step of the user of claim 7, further comprising
   filtering, by the processor, the DC component from each of the respective signals indicative of movement of the user; and
   outputting, by the processor, the AC component of each of the three signals indicative of movement of the user for further processing.

11. The step detection method configured to detect a step of the user of claim 10, further comprising:
   subtracting, by the processor, each of the AC components from a respective one of the signals indicative of movement of the user; and
   outputting, by the processor, the DC components of the three signals indicative of movement of the user for further processing.

12. The step detection method configured to detect a step of the user of claim 7, further comprising:
   calculating, by the processor, the AEE over the integration period by:
      (1) calculating the square root of the sum of the squares of the AC components for each discrete sample during the integration period; and
      (2) summing the calculated values for each discrete sample during the integration period, wherein the sum is the AEE.

13. The step detection method configured to detect a step of the user of claim 7, wherein the periodic calculating of AEE is performed for each sample of the three measured signals indicative of movement of the user.

* * * * *